(12) United States Patent
Yamazaki et al.

(10) Patent No.: US 8,601,009 B2
(45) Date of Patent: Dec. 3, 2013

(54) COMMUNICATION SYSTEM

(75) Inventors: Shunpei Yamazaki, Tokyo (JP); Jun Koyama, Kanagawa (JP)

(73) Assignee: Semiconductor Energy Laboratory Co., Ltd., Atsugi-shi, Kanagawa-ken (JP)

( * ) Notice: Subject to any disclaimer, the term of this patent is extended or adjusted under 35 U.S.C. 154(b) by 11 days.

(21) Appl. No.: 12/471,984

(22) Filed: May 26, 2009

(65) Prior Publication Data

US 2009/0239580 A1 Sep. 24, 2009

Related U.S. Application Data

(63) Continuation of application No. 09/852,266, filed on May 10, 2001, now abandoned.

(30) Foreign Application Priority Data

May 11, 2000 (JP) ................................ 2000-138095

(51) Int. Cl.
*G06F 17/30* (2006.01)
*G06F 7/00* (2006.01)

(52) U.S. Cl.
USPC .......................................... 707/755; 707/756

(58) Field of Classification Search
USPC ................................................ 707/755, 756
See application file for complete search history.

(56) References Cited

U.S. PATENT DOCUMENTS

| | | | |
|---|---|---|---|
| 4,993,068 A | 2/1991 | Piosenka et al. | |
| 5,280,527 A | 1/1994 | Gullman et al. | |
| 5,764,789 A | 6/1998 | Pare, Jr. et al. | |
| 5,845,016 A | 12/1998 | Matsui et al. | |
| 5,915,034 A * | 6/1999 | Nakajima et al. | 382/124 |
| 5,929,845 A | 7/1999 | Wei et al. | |
| 5,930,804 A | 7/1999 | Yu et al. | |
| 5,966,112 A | 10/1999 | Katagiri et al. | |
| 6,028,581 A | 2/2000 | Umeya | |
| 6,031,942 A * | 2/2000 | Nakayama | 382/284 |
| 6,070,796 A | 6/2000 | Sirbu | |
| 6,075,983 A | 6/2000 | Kumagai | |
| 6,144,757 A | 11/2000 | Fukuzumi | |
| 6,175,922 B1 | 1/2001 | Wang | |
| 6,182,076 B1 | 1/2001 | Yu et al. | |
| 6,213,391 B1 * | 4/2001 | Lewis | 235/380 |

(Continued)

FOREIGN PATENT DOCUMENTS

| | | |
|---|---|---|
| DE | 19511386 | 5/1996 |
| DE | 19809006 | 9/1999 |

(Continued)

OTHER PUBLICATIONS

Office Action (EP Application No. 04 027 785.7) mailed Feb. 1, 2008; 5 pages.

(Continued)

*Primary Examiner* — Kuen Lu

(74) *Attorney, Agent, or Firm* — Fish & Richardson P.C.

(57) ABSTRACT

A communication system capable of easily distinguishing a user includes means for storing reference living body information, means for reading collation living body information of the user, means for collating the collation living body information with the reference living body information and means for sending a notice of coincidence as data to a mating party when the collation result proves coincident.

20 Claims, 14 Drawing Sheets

(56) References Cited

U.S. PATENT DOCUMENTS

| | | | |
|---|---|---|---|
| 6,219,792 | B1 | 4/2001 | Bouthillier et al. |
| 6,219,793 | B1 | 4/2001 | Li et al. |
| 6,327,376 | B1 | 12/2001 | Harkin |
| 6,456,279 | B1 | 9/2002 | Kubo et al. |
| 6,476,374 | B1 | 11/2002 | Kozlowski et al. |
| 6,484,260 | B1 | 11/2002 | Scott et al. |
| 6,539,101 | B1 | 3/2003 | Black |
| 6,587,873 | B1 | 7/2003 | Nobakht et al. |
| 6,594,505 | B1 | 7/2003 | Ishii |
| 6,657,538 | B1 | 12/2003 | Ritter |
| 6,751,733 | B1 | 6/2004 | Nakamura et al. |
| 6,751,734 | B1 | 6/2004 | Uchida |
| 7,030,860 | B1 * | 4/2006 | Hsu et al. .................. 345/173 |
| 7,751,600 | B2 | 7/2010 | Yamazaki et al. |
| 7,836,491 | B2 | 11/2010 | Yamazaki et al. |
| 2001/0000045 | A1 | 3/2001 | Yu et al. |
| 2001/0031074 | A1 | 10/2001 | Yamazaki et al. |
| 2001/0047479 | A1 | 11/2001 | Bromba et al. |
| 2002/0001400 | A1 | 1/2002 | Yamazaki et al. |
| 2002/0052192 | A1 | 5/2002 | Yamazaki et al. |
| 2004/0177097 | A1 | 9/2004 | Yu et al. |
| 2010/0104147 | A1 | 4/2010 | Yamazaki et al. |
| 2011/0035798 | A1 | 2/2011 | Yamazaki et al. |

FOREIGN PATENT DOCUMENTS

| | | | |
|---|---|---|---|
| DE | 20008345 | | 8/2000 |
| EP | 0923018 | A2 * | 12/1998 |
| EP | 0 986 209 | | 3/2000 |
| EP | 0 994 439 | | 4/2000 |
| EP | 1 237 091 | A1 | 9/2002 |
| FR | 593 368 | | 2/1925 |
| GB | 2 148 569 | | 5/1985 |
| GB | 2 229 844 | | 10/1990 |
| GB | 2 312 040 | | 10/1997 |
| GB | 2 315 954 | | 2/1998 |
| GB | 2 348 309 | A | 9/2000 |
| JP | 11-085705 | A | 3/1999 |
| JP | 11-203041 | | 7/1999 |
| JP | 11-327727 | | 11/1999 |
| JP | 11-327727 | A | 11/1999 |
| JP | 11-345264 | | 12/1999 |
| JP | 2000-059501 | | 2/2000 |
| JP | 2000-276445 | | 10/2000 |
| JP | 2000-516746 | A | 12/2000 |
| JP | 2001-244926 | A | 9/2001 |
| JP | 2001-005945 | | 12/2001 |
| WO | WO 98/11750 | | 3/1998 |
| WO | WO 98/40962 | | 9/1998 |
| WO | WO 98/50875 | | 11/1998 |
| WO | 98/057247 | A1 | 12/1998 |
| WO | WO 99/24938 | | 5/1999 |
| WO | WO 99/28701 | | 6/1999 |
| WO | WO 00/17823 | | 3/2000 |

OTHER PUBLICATIONS

Search Report (EP Application No. 04 027 785.7) mailed Dec. 21, 2004, 3 pages.

A. Stockel, "Securing Data and Financial Transactions," 0-7803-26727-X/95, IEEE, pp. 397-401, 1995.

Hyun-Jung Kim, "Biometrics, Is it a Viable Proposition for Identity Authentication and Access Control?" Computers & Security, vol. 14, No. 3, pp. 205-214, 1995.

T. Kobayashi, "A Fingerprint Image Recognition Method for Network User Identification," Nippon Telegraph and Telephone; 0-8186-2812-X/92, IEEE, pp. 369-372, 1992.

* cited by examiner

COMMUNICATION SYSTEM

CROSS-REFERENCE TO RELATED APPLICATIONS

This application is a continuation of U.S. application Ser. No. 09/852,266, filed May 10, 2001, which claims the benefit of a foreign priority application filed in Japan on May 11, 2000, as Serial No. 2000-138095, both of which are incorporated by reference.

BACKGROUND OF THE INVENTION

1. Field of the Invention

This invention relates to a communication system. More particularly, this invention relates to a communication system for executing authentication (identifying) by using living body information (biological information).

2. Description of the Related Art

A communication technology that connects an authentication (identification) apparatus such as a cellular telephone, a personal computer, a portable information terminal, or the like, through the Internet has made a remarkable progress in recent years. For Internet connection in business concerns and homes, it is customary to connect a fixed type personal computer to a telephone line. Particularly recently, various information exchanges have become possible as a cellular telephone system such as so-called i-mode capable of being connected easily to the Internet has become wide spread.

Mail-order business and stock trade using a communication network such as the Internet has drawn an increasing attention nowadays because of its convenience that transactions can be made at one's home. When making a deal with a mating party by using an authentication apparatus, however, authentication as to whether or not a communicating party is an authentic party is practically difficult. Therefore, there is the possibility that the third party other than the authentic person communicates as the user with the mating party under the disguise of the authentic person.

Under these circumstances, it has been desired to further improve reliability of authentication that the user is the authentic person.

FIG. 14 shows a flow of a conventional authentication processing. First, the user uses an authentication apparatus such as a cellular telephone and connects it to the Internet. The user then transmits a password such as password number as data for authentication to the mating party under a designated condition. Receiving the password for authentication as the data, the mating party collates a password of the authentic person registered thereto in advance with the password sent from the user and confirms whether or not they are coincident. The user is authenticated as the authentic person when the passwords coincide and is not authenticated, when they do not.

After collation is completed, the mating party sends a collation end signal representative of authentication approval/rejection as information as data to the user. When the user is not authenticated as the authentic person, the user again transmits the password as the data to the mating party. When the user is authenticated, the authentication operation is finished at the point when the user receives the collation end signal, and communication is then started.

Incidentally, the term Communication used herein means transmission/reception of the intended information that is executed after the authentication operation is completed.

As described above, the conventional authentication operation confirms whether or not the user is the authentic person by collating the number the user transmits to the mating party with the password of the authentic person registered in advance to the mating party in order to prevent the third party other than the authentic person from communicating as the user with the mating party under the disguise of the authentic person.

The communication system using the conventional authentication apparatus is not free from the following problems.

The possibility of the leak of the password to the third party cannot be denied. When the password leaks to the third party, the conventional authentication operation cannot confirm whether or not the user is the authentic person.

In addition, it is afraid that the authentic person forgets the password. In such the case, the authentic person must ask the mating party, or often re-write the password. Thus, it should be very troublesome.

In the conventional authentication operation, the user must transmit the password as the data to the mating party, and must receive the collation end signal from the mating party. When the user sends a wrong password to the mating party, the user must again send the correct password to the mating party. In other words, transmission/reception of the data must be carried out at least twice between the mating party and the user.

When the number of times of data transmission/reception between the user and the mating party, the cost necessary for authentication increases. When the number of times of data transmission/reception is great, the possibility is high that a line between the user and the mating party is cut off during data transmission/reception for some reason or other. When the line is cut off during data transmission/reception, it becomes necessary to start once again the authentication operation from the beginning and this is troublesome and complicated.

SUMMARY OF THE INVENTION

The present invention is directed to solve the problems described above.

In the present invention, the authentication (identification) operation is executed on only the user side, and the notice of the finish of authentication is transmitted as data to the mating party. Confirmation (authentication) as to whether or not the user is the authentic person is made as living body information (biological information) of the user (collation living body information) is collated with living body information of the authentic person (reference living body information).

In the present specification, the term living body information (biological information) means bodily features naturally inherent to a person and also information that enables a person to be individually distinguished. Typical living body information includes the fingerprint, the palm print and voiceprint, but the present invention is not particularly limited to them. In other words, the present invention can use those bodily features that are naturally inherent to a person and enables the person to be individually distinguished, for the authentication operation as the living body information.

When the living body information of the user does not coincide with that of the authentic person as a result of collation, the user again executes collation of the living body information between the user and the authentic person. When the living body information of the user coincides with that of the authentic person, the user transmits a notice of the finish of authentication to the mating party as the data and finishes the authentication operation.

After the authentication operation is completed and the mating party confirms the user as the authentic person, the intended communication is started with the mating party.

When the living body information of the user does not coincide with the living body information of the authentic person in the authentication operation described above, the living body information of the user can be again collated with the living body information of the authentic person. When collation is continuously carried out at least n times (n: natural number) and yet does not prove coincident, the notice may be given automatically to the mating party to the effect that the collation result is not coincident.

A plurality of living body information of the authentic person (reference living body information) may exist. For example, the authentication operation can be executed by using both fingerprint and voiceprint. A plurality of fingerprints can be used as the living body information of the authentic person (reference living body information).

A plurality of living body information of the user (collation living body information) can be used, too. A plurality of living body information of the same kind or a plurality of living body information of different kinds can be used, as well.

When the reference living body information is re-written, it is necessary to submit any proof evidencing the authentic person to the mating party. Alternatively, the following method may be employed. The authentication operation is executed once and a password necessary for re-writing the reference living body information is sent as data to the mating party. When this password proves coincident on the mating party side, the reference living body information is then re-written.

The authentication operation described above is not always be limited to authentication between the user and the mating party. When a manager who manages communication between the user and the mating party exists, for example, communication between the user and the mating party may be started after the notice of the end of authentication that authenticates the user as the authentic person is sent to the manager.

Incidentally, the term mating party or manager in this specification means the party that manages the communication made between the user of the authentication apparatus and the mating party. More concretely, the term includes also a provider. However, the mating party or the manager used herein is not particularly limited thereto but may include the party that controls the communication made between the user and the mating party.

When the manager managing the communication between the user and the mating party exists, the notice may be automatically given to the manager to the effect that collation does not prove coincident even after it is made continuously more than n times (n: natural number).

When the reference living body information is re-written in this case, it is necessary to submit any proof evidencing the user as the authentic person to the manager. The following method may be employed, too. After the authentication operation is conducted once, the password necessary for rewriting the living body information is sent as data to the manager. When the passwords prove coincident on the manager side, the reference living body information can then be re-written.

Since the present invention executes the authentication operation by using the living body information as described above, the present invention can eliminate the possibility of leak of the password to the third party other than the authentic person. Therefore, the present invention can improve reliability by the authentication operation for authenticating the user as the authentic person.

Because the number of times of the data exchange operation between the user and the mating party (or the manager) can be restricted during the authentication operation, the cost necessary for the data transmission/reception can be restricted. Even when the communication is cut off for some reason or other, the present invention can avoid the troublesome operation of repeating again the authentication operation from the beginning.

Because the present invention executes the authentication operation by using the living body information of the user, the present invention can eliminate the necessity of the user to inquire of the mating party the password or to frequently re-write the password when the user forgets the password.

The living body information generally has a greater data quantity than the password. However, because the present invention need not send the living body information of the authentic person or the user as the data to the mating party (or the manager), the length of the time necessary for transmitting/receiving the data to and from the mating party (or the manager) can be shortened and the cost can be restricted, too.

In the present invention, the mating party (or the manager) need not store the reference living body information of all persons who execute the authentication operation. Therefore, even though the information quantity of the living body information is greater than the password, the load to the mating party (or the manager) does not become great. Because the reference living body information is stored on the individual basis, the number of the reference living body information (here, all the living body information of the same person is counted as 1) leaking to the third party when security is broken can be kept at a smaller value than when the reference living body information of all the persons who execute the authentication operation is stored in the mating party (or the manager).

The construction of the present invention will be hereinafter illustrated.

The present invention provides a communication system for distinguishing a user, including means for storing reference living body information (biological information) means for reading collation living body information of the user; means for collating the collation living body information with the reference living body information; and means for sending a notice of coincidence as data to a mating party when the collation result proves coincident.

The present invention provides a communication system for distinguishing a user, including means for storing n reference living body information; means for reading n collation living body information of the user; means for collating the n collation living body information with the n reference living body information; and means for sending a notice of coincidence as data to a mating party when all of the collation results prove coincident.

The present invention provides a communication system for distinguishing a user, including means for storing n reference living body information; means for reading m collation living body information of the user; means for collating the m collation living body information with the n reference living body information; and means for sending a notice of coincidence as data to a mating party when at least one of the n reference living body information coincides with at least one of the m collation living body information.

The present invention provides a communication system for distinguishing a user, including means for storing a plurality of kinds of reference living body information; means for reading a plurality of kinds of collation living body information of the user; means for collating the plurality of collation living body information with the plurality of reference living body information; and means for sending a notice of coincidence as data to a mating party when the plurality of kinds of collation living body information wholly coincide with the plurality of kinds of reference living body information.

The present invention provides a communication system for distinguishing a user, including means for storing n reference living body information of a plurality of kinds; means for reading m collation living body information of a plurality of kinds of a user; means for collating the m collation living body information with the n reference living body information; and means for sending a notice of coincidence as data to a mating party when at least one of each kind of collation living body information among the plurality of kinds of collation living body information coincides with at least one of each kind of reference living body information among the n reference living body information.

The present invention provides a communication system for distinguishing a user, including means for storing n reference living body information of a plurality of kinds; means for reading m collation living body information of a plurality of kinds of a user; means for collating the m collation living body information with the n reference living body information; and means for sending a notice of coincidence as data to a mating party when all of the plurality of kinds of collation living body information coincide with all of the n reference living body information.

The present invention provides a communication system for distinguishing a user, including means for storing reference living body information; means for reading collation living body information of the user; means for collating the collation living body information with the reference living body information; means for sending a notice of coincidence as data to a manager when the collation result proves coincident; wherein communication between the user and the mating party is started through the manager after the mating party receives the notice of coincidence as data.

The present invention provides a communication system for distinguishing a user, including means for storing reference living body information; means for reading collation living body information of the user; means for collating the collation living body information with the reference living body information; means for sending a notice of coincidence as data to a manager when the collation result proves coincident; and means for causing the manager to send the notice of coincidence as data to a mating party; wherein communication between the user and the mating party is started through the manager after the mating party receives the notice of coincidence as data.

The present invention provides a communication system for distinguishing a user, including means for storing reference living body information; means for reading collation living body information of the user; means for collating the collation living body information with the reference living body information; means for sending a notice of coincidence as data to a manager when the collation result proves coincident; and means for causing the manager to send the notice of coincidence as data to a mating party; wherein communication between the user and the mating party is directly started after the mating party receives the notice of coincidence as data.

In the communication system described above, identification of the user is requested only when transactions are conducted between the user and the mating party and the condition set to the mating party is satisfied.

The present invention provides a communication system for distinguishing a user, including means for storing reference living body information; means for reading collation living body information of the user; means for collating the collation living body information with the reference living body information; and means for sending a notice of coincidence as data to a mating party when the collation result proves coincident; wherein a password is sent as data to the mating party after the notice of collation is sent to the mating party, and the reference living body information is re-written when the password is authenticated as correct on the mating party side.

The present invention provides a communication system for distinguishing a user, including means for storing n reference living body information; means for reading n collation living body information of the user; means for collating the n collation living body information with the n reference living body information; and means for sending a notice of coincidence as data to a mating party when the collation results wholly prove coincident; wherein a password is sent as data to the mating party after the notice of collation is sent to the mating party, and the n reference living body information is re-written when the password is authenticated as correct on the mating party side.

The present invention provides a communication system for distinguishing a user, including means for storing n reference living body information; means for reading m collation living body information of the user; means for collating the m collation living body information with the n reference living body information; and means for sending a notice of coincidence as data to a mating party when at least one of the n reference living body information coincides with at least one of the m collation living body information; wherein a password is sent as data to the mating party after the notice of collation is sent to the mating party, and the n reference living body information is re-written when the password is authenticated as correct on the mating party side.

The present invention provides a communication system for distinguishing a user, including means for storing a plurality of kinds of reference living body information; means for reading a plurality of kinds of collation living body information of the user; means for collating the plurality of kinds of collation living body information with a plurality of kinds of the reference living body information; and means for sending a notice of coincidence as data to a mating party when a plurality of kinds of the collation living body information wholly coincide with a plurality of kinds of reference living body information; wherein a password is sent as data to the mating party after the notice of collation is sent to the mating party, and the a plurality of kinds of reference living body information is re-written when the password is authenticated as correct on the mating party side.

The present invention provides a communication system for distinguishing a user, including means for storing n reference living body information of a plurality of kinds; means for reading m collation living body information of a plurality of kinds of the user; means for collating the m collation living body information with the n reference living body information; and means for sending a notice of coincidence as data to a mating party when at least one of the collation living body information of each kind among the plurality of kinds coincides with at least one of n reference living body information of each kind; wherein a password is sent as data to the mating party after the notice of collation is sent to the mating party, and the plurality of kinds of the reference living body information is re-written when the password is authenticated as correct on the mating party side.

The present invention provides a communication system for distinguishing a user, including means for storing n reference living body information of a plurality of kinds; means for reading m collation living body information of a plurality of kinds of the user; means for collating the m collation living body information with the n reference living body information; and means for sending a notice of coincidence as data to a mating party when all of the plurality of kinds of collation living body information coincide with all of the n collation living body information; wherein a password is sent as data to the mating party after the notice of collation is sent to the mating party, and the plurality of kinds of reference living body information is re-written when the password is authenticated as correct on the mating party side.

The present invention provides a communication system for distinguishing a user, including means for storing reference living body information; means for reading collation living body information of the user; means for collating the collation living body information with the reference living body information; and means for sending a notice of coincidence as data to a manager when the collation result proves coincident; wherein a password is sent as data to the manager after the notice of collation is sent to the manager, and the reference living body information is re-written when the password is authenticated as correct by the manager.

The reference living body information may be a fingerprint, a palm print or a voiceprint.

The collation living body information may be a fingerprint, a palm print or a voiceprint.

The palm print may be a palm print of the whole palm or palm print of a part of the palm of a hand.

The storing means may be a flash memory.

The reading means may be a photodiode or a charge coupled device (CCD).

The present invention can use a portable information terminal, a cellular telephone or a personal computer.

DESCRIPTION OF THE PREFERRED EMBODIMENTS

Embodiment Mode

Figure 1:
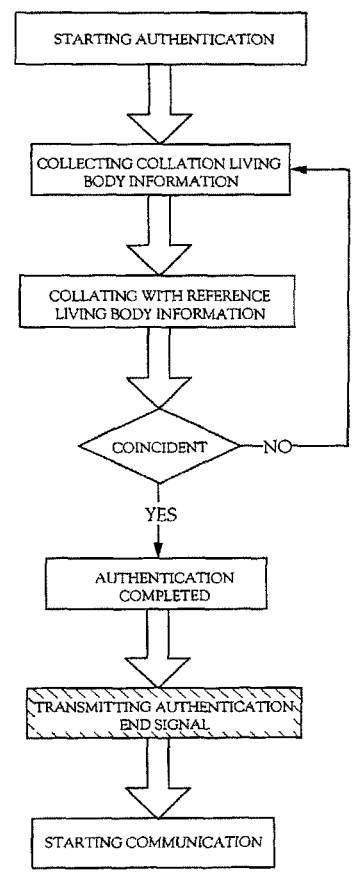
FIG. 1 is a flowchart showing a processing flow of a communication system according to the present invention.

FIG. 1 shows a flow of a communication system according to the present invention. When authentication is started, an apparatus for executing authentication (authentication apparatus) collects living body information of a user. The user controls the authentication apparatus to collect the living body information. A program may be arranged in advance so that the user can start collecting the living body information by merely pushing one operation key. It is also possible to constitute the authentication apparatus so that it can automatically start collecting the living body information when its power source is turned on.

Collection of the living body information can be made by means of a line sensor or an area sensor using a CCD or a photo-diode, or a microphone.

The authentication apparatus stores beforehand the living body information of a person (reference living body information). The reference living body information is stored in a built-in memory of the authentication apparatus, such as a non-volatile memory.

The living body information (collation living body information of the user) thus collected is collated with the personal living body information (reference living body information) stored in advance in the authentication apparatus. When the collation living body information coincides with the reference living body information, the user can be authenticated as the authentic person authorized to make the intended communication.

When the collation result does not prove coincident, the authentication apparatus again collects the living body information of the user, and collates again the collation living body information so acquired with the reference living body information.

The user can arbitrarily set the number of times of repetition of collation of the living body information. For example, the user may set the upper limit number of times of repetition in one authentication operation to n (n: arbitrary natural number). When the collation result does not prove coincident even after the collation operation is carried out continuously n times, the authentication apparatus may raise an alarm. When the collation result does not prove coincident even after collation is repeated continuously n times, the failure of collation may be automatically notified to persons other than the user or to an apparatus other than the authentication apparatus.

After authentication is completed, a signal having information representative of the finish of authentication (authentication end signal) is transmitted to a mating party with which communication is to be made. Since authentication has already been finished in this case, the exchange of the living body information need not be made newly with the mating party. In other words, it is only necessary for the mating party to receive the authentication end signal from the authentication apparatus.

Authentication is finished when the mating party receives the authentication end signal. After authentication is completed, the user and the mating party start the intended communication. The intended communication is not limited to business communication for profit making such as transactions. This communication made between the user and the mating party can transmit all kinds of intentions and information.

The authentication apparatus in the present invention must essentially have the three functions of collecting the living body information of the user, collating the living body information and transmitting the authentication end signal. One authentication apparatus may have all of these functions, or a plurality of apparatuses may altogether attain these three functions. In the latter case, a plurality of apparatuses will be altogether referred to as the authentication apparatus.

Next, the fingerprint and the palm print will be explained among the living body information used in the communication system according to the present invention.

Figure 2:
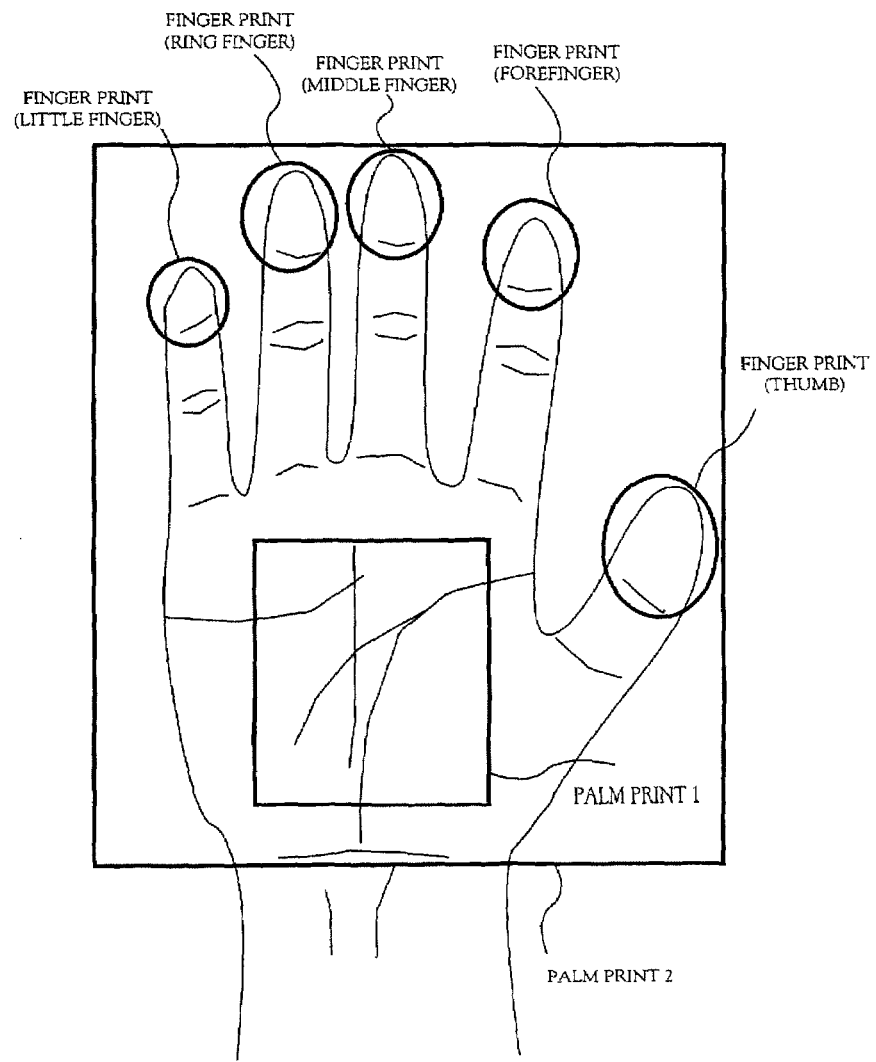
FIG. 2 is a schematic view showing the position of a palm print or a fingerprint to be read of the present invention.

FIG. 2 depicts a right hand of a person. The living body information read by the authentication apparatus includes the palm print 1 as a part of the palm of the hand, the pal print 2 as an entire of the palm, the fingerprint of a thumb, the fingerprint of a forefinger, the fingerprint of a middle finger and the fingerprint of a ring finger or a little finger. It is also possible to use the palm print of the left hand, or the palm prints of both of right and left hands.

The palm print 1 as a part of the palm of the hand, the palm print 2 as the whole palm of the hand, the fingerprint of the thumb, the fingerprint of the forefinger, the fingerprint of the middle finger and the fingerprints of the ring and little fingers are inherent to an individual. Therefore, the abuse of the authentication apparatus by the third party can be prevented.

Only one kind, or a plurality of kinds, of the living information may be used for the communication system according to the present invention. A single or a plurality of living information of the same kind can be used, too. For example, a plurality of fingerprints of the same thumb can be use as a plurality of kinds of living body information. A plurality of living body information of different kinds can be used. For example, a plurality of fingerprints of the same little finger and a voiceprint can be used in combination as the living body information.

Next, explanation will be given concretely on the case where collation is conducted by using a plurality of living body information of the same kind.

Figure 3A:
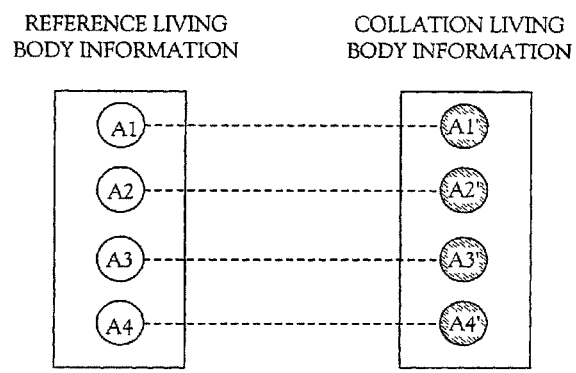
FIGS. 3A and 3B are relational diagrams of collation of living boy information of the present invention.
Figure 3B:
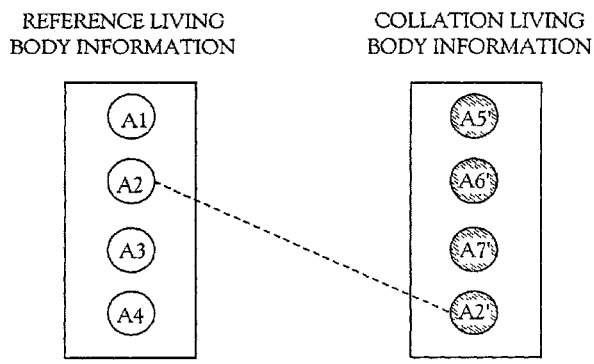

FIGS. 3A and 3B are relational diagrams when a plurality of reference living body information is used to perform collation. FIG. 3A shows an example where authentication is given when all of four reference living body information (A1, A2, A3, A4) and four collation living body information (A1', A2', A1', A4', coincide with one another.

As shown in FIG. 3A, A1 and A1', B1 and B1', C1 and C1', and D1 and D1', are coincident, respectively. In this way, authentication is given only when a plurality of reference living body information and a plurality of collation living body information all coincide with one another. In consequence, reliability of authentication of the user as the authentic person can be improved.

Incidentally, the number of reference living body information and collation living body information is not limited to 4 but is arbitrary.

FIG. 3B shows the case where authentication is given when any one of four reference living body information (A1, A2, A3, A4) coincides with any one of four collation living body information (A5', A6', A7', A8', A2').

As shown in FIG. 3B, A2 and A2' coincide with each other, but A1, A3, A4 and A5', A6', A7', do not, respectively. The number of times of collection of collation living body information can be restricted by giving authentication only when any one of a plurality of reference living body information and any one of a plurality of collation living body information coincide with each other. The authentication process becomes easier, too, in this case.

Incidentally, the number of the reference living body information and collation living body information is not limited to 4 but is arbitrary. FIG. 3B shows the case where authentication is given only when any one of a plurality of reference living body information coincides with any one of a plurality of collation living body information, but the number of coincidence is not limited to 1, but can be arbitrarily set by the operator.

Figure 4A:
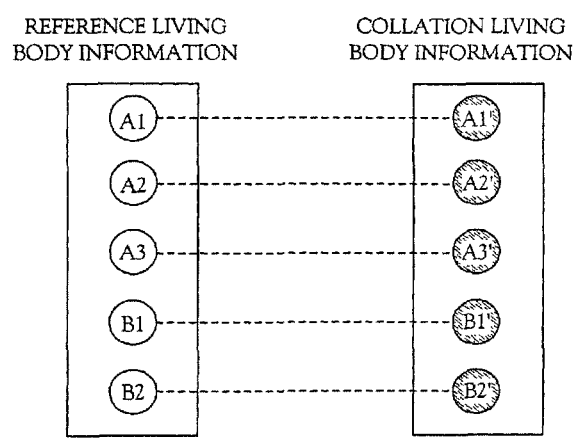
FIGS. 4A and 4B are relational diagrams of collation of living body information of the present invention.
Figure 4B:
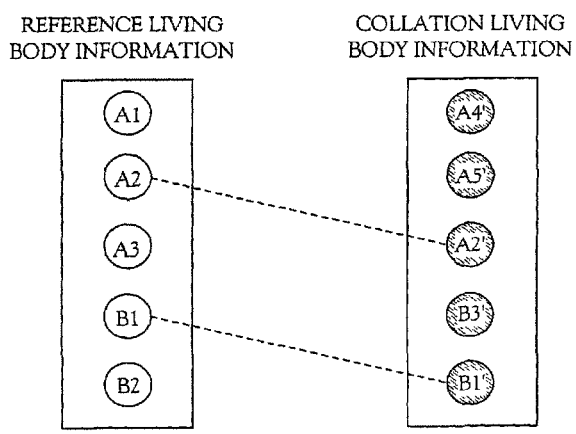

FIGS. 4A and 4B show a relational diagrams of collation when using a plurality of kinds of reference living body information. FIG. 4A shows the case where authentication is given when two kinds of reference living body information (A1, A2, A3, B1, B2) coincide completely with two kinds of collation living body information (A1', A2', A3', B1', B2'). In this way, authentication is given only when a plurality of kinds of reference living body information wholly coincides with a plurality of kinds of collation living body information, and reliability of the user as the authentic person can be improved.

As shown in FIG. 4A, A1 and A1', A2 and A2', A3 and A3', B1 and B1', and B2 and B2' coincide with one another, respectively. Reliability of authenticity of the user as the authentic person can be further improved by judging authenticity only when a plurality of kinds of reference living body coincide completely with a plurality of kinds of collation living body information.

Incidentally, the number of kinds of both reference living body information and collation living body information is not limited to 2, but the number of kinds of living body information is arbitrary. The number of each kind of the reference living body information and the collation living body information is arbitrary, too.

FIG. 4B shows the case where authentication is given when any one of three reference living body information (A1, A2, A3) coincides with any one of collation living body information (A4', A5', A2') and either one of two reference living body information (B, B2) coincides with either one of collation living body information (B3', B1').

As shown in FIG. 4B, A2 coincides with A2' and B1 coincides with B1'. However, A1, A3, B2 and A4', A5', B3' do not coincide with each other, respectively. In this way, reliability of authentication of the user as the authentic person can be improved by granting authentication only when any one of the reference living body information of each kind among a plurality of kinds of reference living body information used coincides with any one of the collation living body information.

Incidentally, the number of kinds of the reference living body information and the collation living body information is not limited to 2, and the number of kinds of living body information is arbitrary. The number of each kind of the reference living body information and the collation living body information is arbitrary, too. FIG. 4B shows the case where authentication is given only when any one of the reference living body information coincides for each kind with any one of a plurality of collation living body information. However, the number of coincidence is not limited to 1, and the user can arbitrarily set the number of coincidence for each kind of living body information.

Next, the processing flow after authentication is completed in the authentication operation described above will be explained in further detail.

Figure 5A:
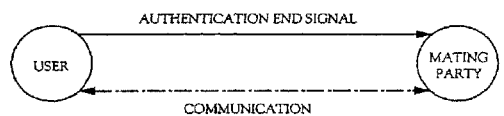
FIGS. 5A to 5D are flowcharts after authentication is completed of the present invention.

FIG. 5A is a relational diagram when authentication and communication are executed only between the user and the mating party. After authentication is completed, the user side (more concretely, the authentication apparatus used by the user) transmits the authentication end signal. The user and the mating party then start the intended communication.

Figure 5B:
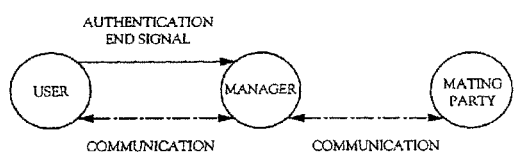

FIG. 5B is a relational diagram when authentication and communication are executed not only between the user and the mating party but also among the user, the mating party and a manager. The manager plays the role of managing communication between the user and the mating party.

The processing flow till completion of authentication is the same as that of the case where it is made between the two parties, i.e., the user and the mating party. After authentication of the user as the authentic person, the user (more concretely, the authentication apparatus used by the user) transmits the authentication end signal to the manager. The user and the mating party then start the intended communication through the manager.

Figure 5C:
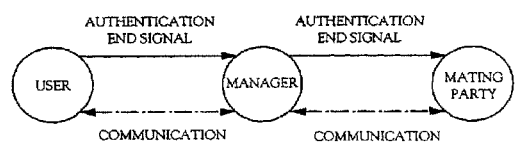

FIG. 5C is a relational diagram when authentication and communication are executed among the three parties, that is, the user, the mating party and the manager.

The processing flow till completion of authentication is the same as the flow when it is executed between the user and the mating party, and its explanation will be omitted. After authentication of the user as the authentic person is completed, the user side (more concretely, the authentication apparatus used by the user) transmits the authentication end signal to the manager. Receiving the authentication end signal from the user side, the manager transmits the authentication end signal to the mating party, too. In this way, the intended communication is started between the user and the mating party through the manager.

Figure 5D:
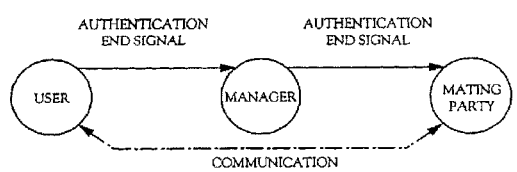

FIG. 5D is a relational diagram when authentication and communication are executed among the three parties, i.e., the user, the mating party and the manager, in the same way as in FIGS. 5B and 5C.

The processing flow till completion of authentication is the same as the flow when it is executed between the user and the mating patty, and its explanation will be omitted. After authentication of the user as the authentic person is completed, the user side (more concretely, the authentication apparatus used by the user) transmits the authentication end signal to the manager. Receiving the authentication end signal from the user side, the manager transmits the authentication end signal to the mating party. The user and the mating party thus execute directly the intended communication without passing through the manager.

Incidentally, when any party (such as the manager) that is involved in authentication and communication other than the user and the mating party exists in the communication system according to the present invention, various combinations of the processing flows may be possible after authentication is completed. The present invention is not limited to the relational diagrams shown in FIGS. 5A to 5D. Any combination may be used so long as the user and the mating parry can start communication when the user transmits the authentication end signal to the other party.

In the communication system according to the present invention, the number of each of the mating party and the manager is not limited to one. In other words, a plurality of mating parties or a plurality of managers may exist.

Since the present invention executes authentication by using the living body information as described above, the present invention can eliminate the possibility that authentication of the user as the authentic person cannot be made as the password leaks to the third party other than the user.

Since the number of times of the data exchange operations can be reduced during authentication between the user and the mating party (or the manager), the cost necessary for transmitting and receiving the data can be decreased, and the trouble that authentication must be again conducted from the beginning when communication is cut off for some reason or other.

Because authentication is executed by using the living body information of the user, the user need not inquire of the mating party the password when he forgets the password, or need not frequently re-write the password.

The living body information generally has a greater information quantity than the password. However, it is not necessary in the present invention to directly transmit the living body information of the person or the user as the data to the mating party (or the manager). Therefore, the time necessary for transmitting and receiving the data to and from the mating party (or the manager) can be shortened, and the cost can be reduced.

In the present invention, it is not necessary to store the reference living body information of all persons who conduct authentication in the mating party (or the manager). Therefore, even though the information quantity of the living body information is greater than that of the password, the load to the mating party (or the manager) does not increase. Since the individual stores the reference living body information, the number of the reference living body information leaking outside when security is broken (in this case, all the living body information secured by the same person is counted as 1) can be kept smaller than when the reference living body information of all persons involved in authentication is stored in the mating party (or the manager).

Hereinafter, examples of the present invention will be explained.

Embodiment 1

This embodiment explains in detail the re-write operation of the reference living body information stored in the authentication apparatus by using the authentication apparatus.

Figure 6:
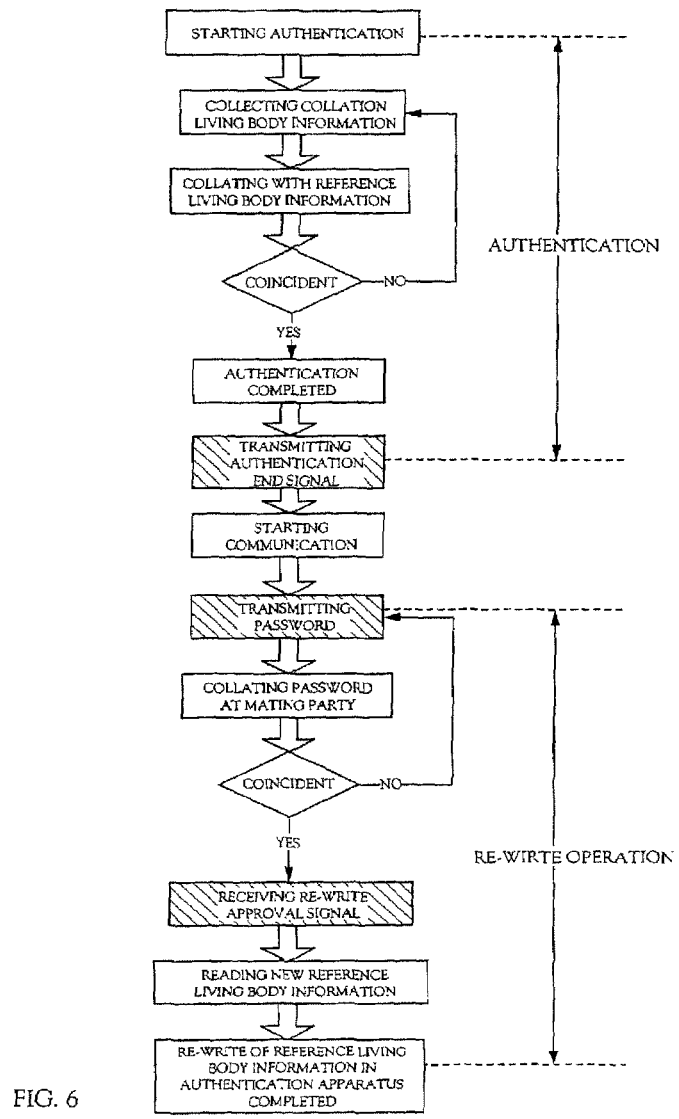
FIG. 6 is a flowchart of a re-write operation for re-writing reference living body information of Embodiment 1.

FIG. 6 shows a flow of the re-write operation of the reference living body information in this example. First, authentication is conducted to authenticate the user as an authentic person. Incidentally, the detailed explanation of authentication has already been given and is hereby omitted.

As authentication is completed and the user and the mating party (or the manager) start communication, the re-write operation is started. The user transmits the password necessary for re-writing the living body information as the data to the mating party.

The re-write operation of the reference living body information cannot be conducted when collation of the password does not prove coincident. In this case, the mating party (or the manager) notifies the user that the password is not coincident. The user can again transmit the password as the data.

In this case, the user can arbitrarily set the number of times of re-transmission of the password in the same way as in the case of collation in authentication. For example, it is possible to prevent repetition of collation in one re-write operation beyond n times (n: arbitrary natural number). The authentication apparatus may be so constituted as to raise an alarm when collation does not continuously prove coincident n times. Furthermore, an arrangement may be employed that automatically notifies persons other than the user or apparatuses other than the authentication apparatus of the failure of collation when collation does not continuously prove coincident n times.

Re-write of the reference living body information is approved when collation of the passwords in the mating party proves coincident. The mating party (or the manager) transmits a re-write approval signal having information representing approval of re-write of the reference living body information to the user.

Receiving the re-write approval signal, the user reads afresh the living body information into the authentication apparatus. The authentication apparatus stores the new reference living body information, and the re-write operation of the reference living body information is completed.

When the reference living body information is re-written in accordance with the flow described above, the possibility that the third party other than the authentic person freely re-writes the reference living body information can be lowered.

Because all the re-write operations can be conducted by using the authentication apparatus, the troubles of the re-write operation of the reference living body information can be suppressed.

Embodiment 2

The construction of the authentication apparatus used in the present invention and its operation will be explained next.

Figure 7:
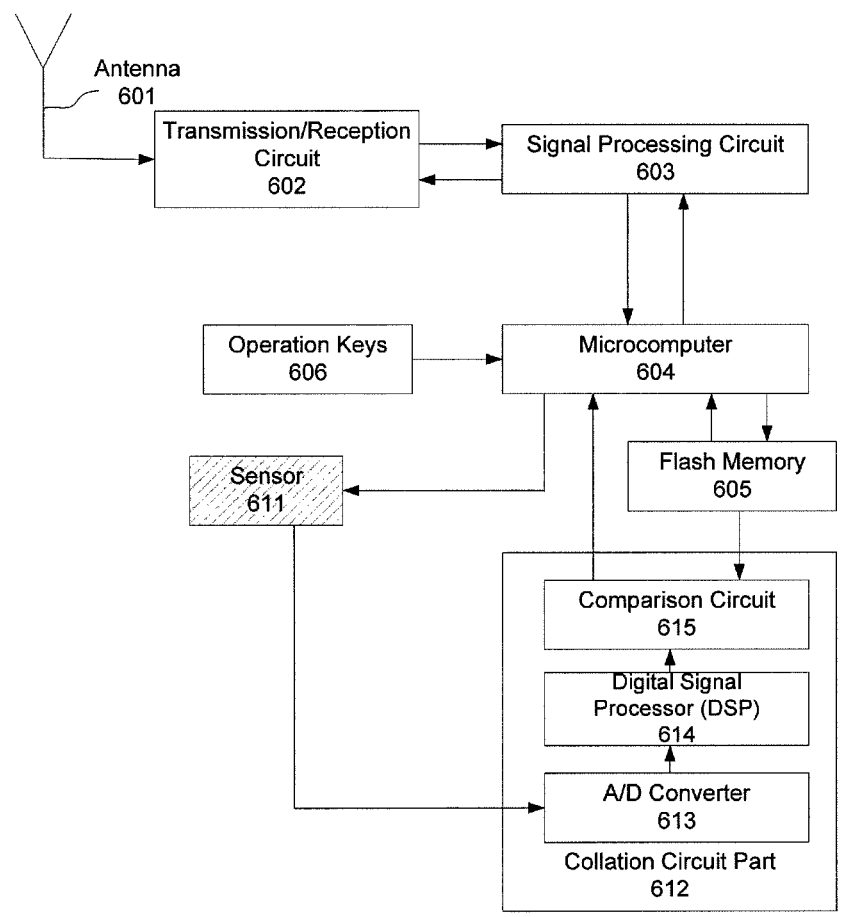
FIG. 7 is a block diagram showing a construction of an authentication apparatus of Embodiment 2.

FIG. 7 is a block diagram of the authentication apparatus according to this embodiment. The authentication apparatus of this embodiment includes an antenna 601, a transmission/reception circuit 602, a signal processing circuit 603 for compressing/expanding signals and encoding them, a microcomputer 604 for control, a flash memory 605, operation keys 606, and so forth. The authentication apparatus further includes a sensor 611 and a collation circuit part 612.

When the operation key 606 is operated, the microcomputer 604 for control controls the sensor 611 and lets it read the living body information of the user. Incidentally, this embodiment uses palm prints or fingerprints as the living body information. The living body information of the user read by the sensor 611 is inputted to the collation circuit part 612.

An A/D converter 613 converts the living body information (collation living body information) of the user inputted to the collation circuit part 612 to digital signals. The living body information of the user thus converted to the digital signals is inputted to a DSP (Digital Signal Processor) 614 and is subjected to signal processing. The term signal processing means more concretely an emphasis processing to stress a changing portion of a density of the image by using a differential filter in order to have the living body information more easily distinguished. The resulting collation living body information is converted to numerical values inside the DSP 614 and is inputted to a comparison circuit 615.

The comparison circuit 615 compares and collates the reference living body information stored in the flash memory 605 with the collation living body information converted to the numerical values inside the DSP 614 and inputted to the comparison circuit 615.

A method of collating the living body information includes a feature collation system that compares and collates the feature of the reference living body information with the feature of the collation living body information, and an image matching system that directly compares the two living body information. The present invention may use either of these systems. Authentication can be conducted more reliably when a plurality of reference living body information is prepared by changing somewhat the posture of a hand, for example.

When coincidence can be observed, the microcomputer 604 for control outputs the authentication end signal, and this signal is outputted from the authentication apparatus through the signal processing circuit 603, the transmission/reception circuit 602 and the antenna 601. The authentication end signal outputted from the authentication apparatus is transmitted to the mating party (or the manager) through the Internet, for example. Incidentally, the authentication end signal outputted from the authentication apparatus may be directly transmitted to the mating party without passing through the Internet.

Embodiment 3

Differences of the construction of the authentication apparatus used in this embodiment and its operation from Embodiment I will be explained.

Figure 8:
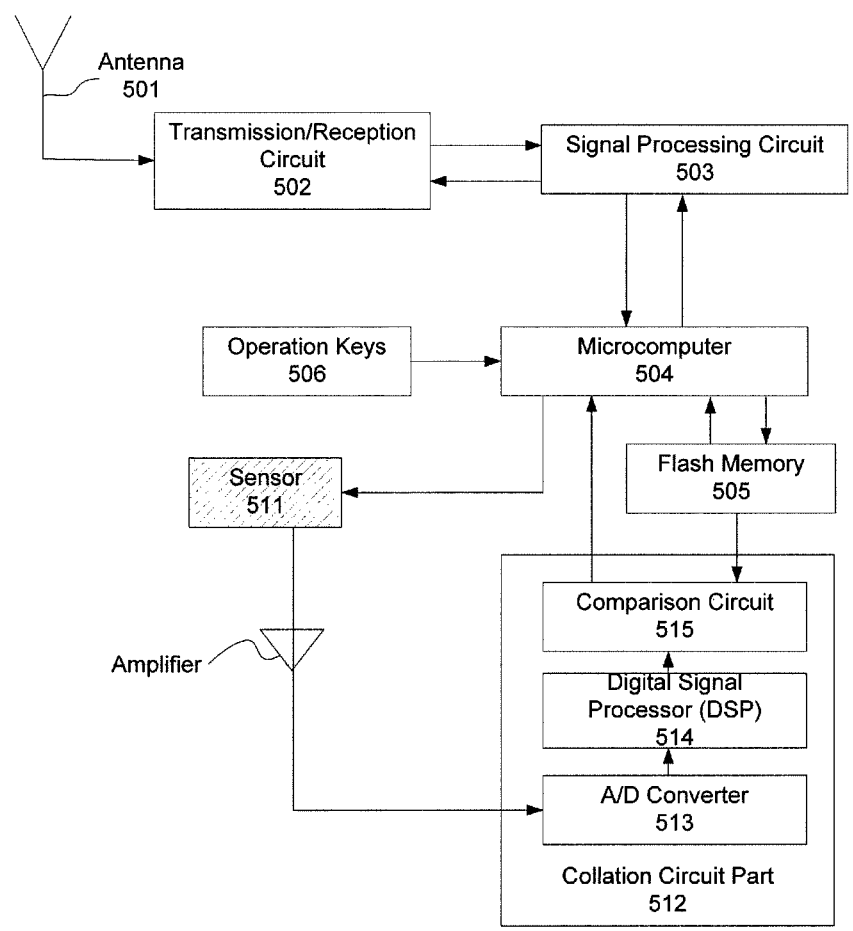
FIG. 8 is a block diagram showing another construction of an authentication apparatus of Embodiment 3.

FIG. 8 is a block diagram of the authentication apparatus of this embodiment. The authentication apparatus includes an antenna 501, a transmission/reception circuit 502, a signal processing circuit 503 for compressing/expanding and encoding signals, a microcomputer 504 for control, a flash memory 505 and operation keys 506. The authentication apparatus further includes a microphone 511, an amplifier 516 and a collation circuit part 512.

When the operation key 506 is operated, the microcomputer 504 for control controls the microphone 511 and lets it read the living body information of the user. Incidentally, this embodiment uses a voiceprint as the living body information. The living body information read by the microphone 511 is amplified by the amplifier 516 and is inputted to the collation circuit part 512.

An A/D converter 513 converts the living body information of the user (collation living body information) inputted to the collation circuit part 512 to digital signals. The collation living body information converted to the digital signals is inputted to a DSP (Digital Signal Processor) 514 and is subjected to signal processing. The term signal processing hereby means more concretely a processing for converting the intensity of sound for each frequency to numerical values by using a band-pass filter, or the like, so that the living body information can be more clearly distinguished. The reference living body information thus converted to the numerical values by the DSP 514 is inputted to the comparison circuit 515.

The comparison circuit 515 compares and collates the reference living body information stored in the flash memory 505 with the collation living body information converted to the numerical values inside the DSP 514 and inputted to the comparison circuit 515.

A method of collating the living body information includes a feature collation system that compares and collates the feature of the reference living body information with the feature of the collation living body information, and an image matching system that directly compares the spectra of these two living body information. The present invention may use either of them. Authentication can be conducted more reliably when a plurality of reference living body information is used instead of only one living body information by somewhat changing pronunciation, for example.

When coincidence is observed, the microcomputer 504 for control outputs the authentication end signal, and this signal is outputted from the authentication apparatus through the signal processing circuit 503, the transmission/reception circuit 502 and the antenna 501. The authentication end signal outputted from the authentication apparatus is transmitted through the Internet, or the like. Incidentally, the authentication end signal may be directly transmitted to the mating party without passing through the Internet.

The construction of this example can be worked in combination with Embodiment 1 or 2.

Embodiment 4

Figure 9:
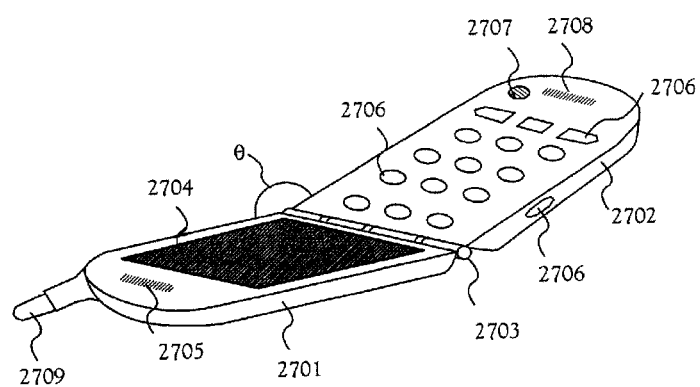
FIG. 9 is an appearance view of a portable information terminal as an example of the authentication apparatus of Embodiment 4.

Next, a portable information terminal as one of the authentication apparatuses used in the present invention will be described. FIG. 9 depicts the portable information terminal used in this embodiment. Reference numeral 2701 denotes a display panel and reference numeral 2702 denotes an operation panel. The display panel 2701 and the operation panel 2702 are connected to each other at a connection part 2703. An angle θ between the surface of the display panel 2701, in which a display 2704 with a built-in sensor is disposed, and the surface of the operation panel 2702, in which a speech input part 2708 is disposed, can be changed arbitrarily.

The display panel 2701 includes a display 2704 having a built-in sensor. The display 2704 having a built-in sensor has the two functions of reading an image and displaying the image. This embodiment uses an EL display for the display 2704 having a built-in sensor.

The portable information terminal shown in FIG. 9 has the function of a telephone unit. The display panel 2701 has a speech output part 2705, and the speech output part 2705 outputs speech.

The operation panel 2702 includes operation keys 2706, a power switch 2707 and a speech input part 2708. Incidentally, the operation keys 2706 and the power switch 2707 are shown disposed separately, but the operation key 2706 may include the power switch 2707. The speech input part 2708 inputs speech.

In FIG. 9, the display panel 2701 is shown having the speech output part 2705 and the operation panel 2702, having the speech input part 2708. However, this embodiment is not particularly limited to this construction. For example, the display panel 2701 may have the speech input part 2708 and the operation panel, the speech output part 2705. Furthermore, both speech output part 2705 and speech input part 2708 can be provided to the display panel 2701 or to the operation panel 2702.

Incidentally, the display 2704 having the built-in sensor may have the function of measuring brightness (luminance) around the portable information terminal and automatically adjusting luminance. The portable information terminal of this embodiment shown in FIG. 9 can measure brightness (luminance) by means of the display 2704 having the built-in sensor. However, it is also possible to dispose a sensor part such as a CCD separately from the display 2704 having the built-in sensor so that the sensor part can measure surrounding luminance and can adjust luminance of the display 2704 having the built-in sensor.

The display 2704 with the built-in sensor in the portable information terminal may be constituted in such a fashion that its brightness becomes automatically high when the power switch is turned on, when the operation key 2706 is operated or when call exists, and becomes automatically low during the speech or after the passage of a predetermined time from the end of the operation of the operation key 2706. In consequence, power consumption of the portable terminal itself can be restricted.

It is also possible to automatically turn off only the display 2704 with the built-in sensor and to prevent display of the image when the operation key 2706 is not operated or when call does not exist for a time longer than a predetermined time.

In this way, power consumption of the portable information terminal itself can be restricted.

The method of using the portable information terminal shown in FIG. 9 will be explained with reference to FIGS. 10 and 11. When authentication is executed by using the portable information terminal shown in FIG. 9, the palm of a hand 2710 is so put as to cover the display 2704 with the built-in sensor. The operation key 2706 is operated to execute authentication. The display 2704 with the built-in sensor reads the lines of the palm of the user and executes authentication.

Figure 10:
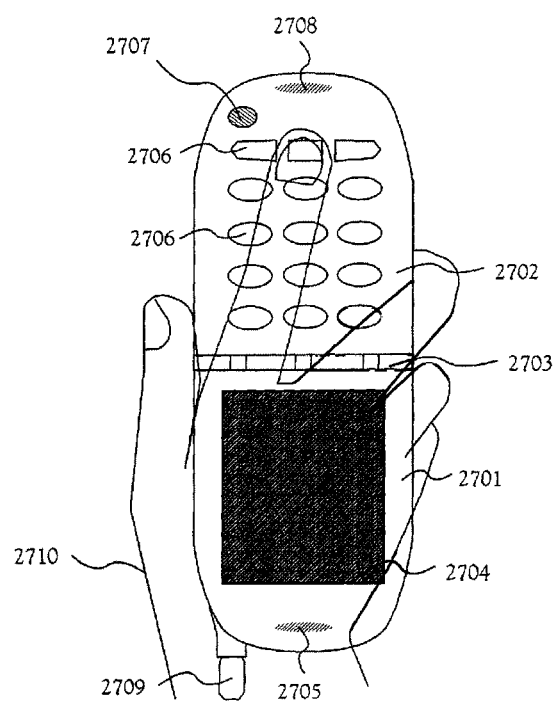
FIG. 10 is a schematic view showing an example of the mode of use of the portable information terminal as an example of the authentication apparatus of Embodiment 4.
Figure 11:
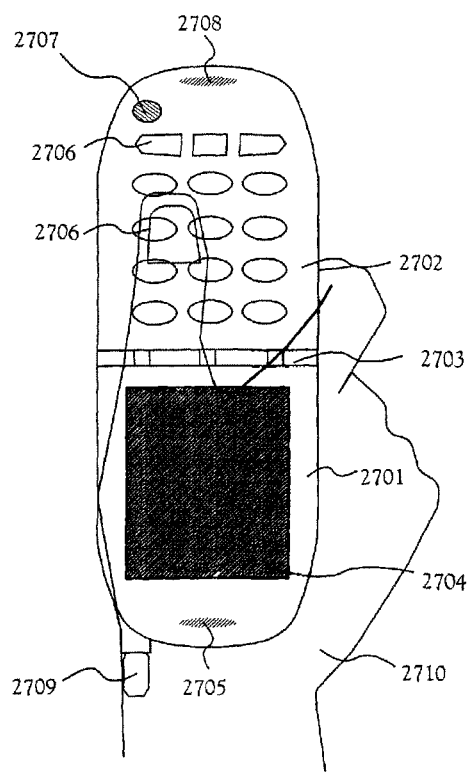
FIG. 11 is a schematic view showing another example of the mode of use of the portable information terminal as an example of the authentication apparatus of Embodiment 4.

FIG. 10 shows the example where the forefinger operates the operation key 2706, but the thumb, too, can operate the operation key 2706 as shown in FIG. 11. Incidentally, the operation key 2706 may be provided to the side surface of the operation panel 2702. Only the forefinger or thumb of one hand (right- or left-handedness) may be used to operate the operation key 2706.

The construction of the portable information terminal shown in FIG. 9 and its operation will be explained.

Figure 12:
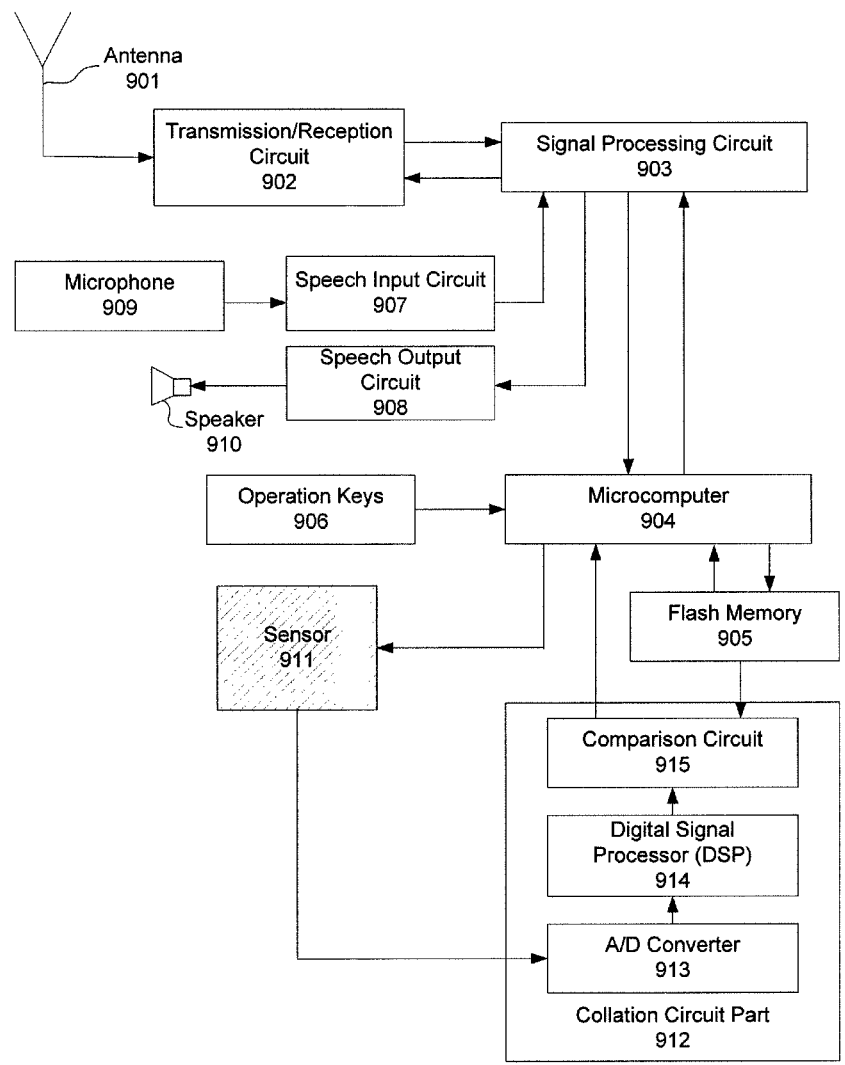
FIG. 12 is a block diagram showing a construction of the portable information terminal as an example of the authentication apparatus of Embodiment 4.

FIG. 12 is a block diagram of the portable information terminal of this embodiment. The portable information terminal includes an antenna 901, a transmission/reception circuit 902, a signal processing circuit 903 for compressing and expanding signals and encoding them, a microcomputer 904 for control, a flash memory 905, operation keys 906, a speech input circuit 907, a speech output circuit 908, a microphone 909 and a speaker 910. The portable information terminal further includes a sensor 911 and a collation circuit part 912.

The speech inputted from the speech input part 2708 is inputted to the microphone 909 and is then inputted as an analog signal to the speech input circuit 907. The analog signal inputted to the speech input circuit 907 is amplified and is then converted to a digital signal. The digital signal is inputted to the signal processing part 903. The digital signal is subjected to compression/expansion and encoding in the signal processing part 903. The transmission/reception circuit 902 changes the frequency of the digital signal. The digital signal is amplified in some cases, and is then transmitted from the antenna 901.

The transmission/reception circuit 902 changes the frequency of the digital signal having the speech information and received by the antenna 901. The digital signal is amplified in some cases, and is inputted to the signal processing part 903. The digital signal inputted to the signal processing part 903 is subjected to compression/expansion and encoding, and is then inputted to the speech output circuit 908. The digital signal inputted to the speech output circuit 908 is converted to the analog signal, is amplified and is outputted from the speaker 910, so that the user can listen to the speech from the speech output part 2708.

When the operation key 906 is operated, the microcomputer 904 for control controls the sensor 911 and lets it read the living body information of the user. Incidentally, this embodiment uses the palm print or the fingerprint as the living body information. The living body information (collation living body information) of the user read by the sensor 911 (concretely, a display with the built-in sensor 911) is inputted to the collation circuit part 912.

An A/D converter 913 converts the collation living body information inputted to the collation circuit part 912 to a digital signal. The collation living body information so converted to the digital signal is inputted to a DSP (Digital Signal Processor) 914 and is subjected to signal processing. The term signal processing means more concretely an emphasis processing to stress a changing portion of a density of the image by using a differential filter in order to have the living body information more easily distinguished. The resulting collation living body information is converted to numerical values inside the DSP 914 and is inputted to a comparison circuit 915.

The comparison circuit 915 compares and collates the reference living body information stored in the flash memory 905 with the collation living body information converted to the numerical values inside the DSP 914 and inputted to the comparison circuit 915.

A method of collating the living body information includes a feature collation system that compares and collates the feature of the reference living body information with the feature of the collation living body information, and an image matching system that directly compares the two living body information. The present invention may use either of these systems. Authentication can be conducted more reliably when a plurality of reference living body information is prepared by changing somewhat the posture of a hand, for example.

When coincidence can be observed, the microcomputer 904 for control outputs the authentication end signal, and this signal is transmitted from the portable information terminal through the signal processing circuit 903, the transmission/reception circuit 902 and the antenna 901. The authentication end signal outputted from the portable information terminal is transmitted through the Internet, for example. Incidentally, the authentication end signal outputted from the portable information terminal may be directly transmitted to the mating party without passing through the Internet.

The authentication apparatus used in the present invention is not particularly limited to the portable information terminal having the construction described in this embodiment. The portable information terminal represented in this embodiment uses the fingerprint or the palm print as the living body information, but may have the construction that uses the voiceprint as the living body information.

Incidentally, this embodiment can be worked in combination with Embodiments 1 to 3

Embodiment 5

This embodiment represents the situation where the present invention is employed. When the intended communication is used for business transactions for profit making such as a deal, the present invention need not be used in some cases where authentication to a high level such as the living body information is not necessary. The present invention is not always necessary in the case where limited amounts of money are transferred.

It is therefore possible to select the necessity of authentication and to selectively conduct authentication only when large amounts of money are transferred. Authentication can thus be made in accordance with the condition of the mating party, or the judgment standard may be set in advance to the control microcomputer of the authentication apparatus so that authentication can be made only when the numerical value exceeds a predetermined value. The authentication end signal may be transmitted to the mating party (or the manager) only when the authentication result is necessary.

Incidentally, this embodiment can be worked in combination with Embodiments 1 to 4.

Embodiment 6

Various electronic appliances can be used as the authentication apparatus to be used in the present invention.

Figure 13A:
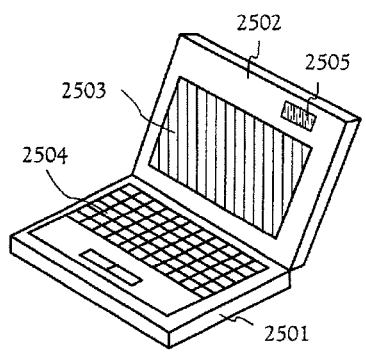
FIGS. 13A and 13B are schematic views showing examples of electronic apparatuses as examples of the authentication apparatus of Embodiment 6.

FIG. 13A depicts a personal computer. The personal computer includes a main body 2501, a casing 2502, a display part 2503, a keyboard 2504, a sensor 2505, and so forth. The present invention can acquire the living body information into the personal computer by using the sensor 2505.

Though this embodiment uses the fingerprint or the palm print as the living body information, a speech input part can be provided to the personal computer so as to utilize the voiceprint as the living body information. Both sensor 2505 and speech input part can be provided to utilize both palm print and voiceprint.

Figure 13B:
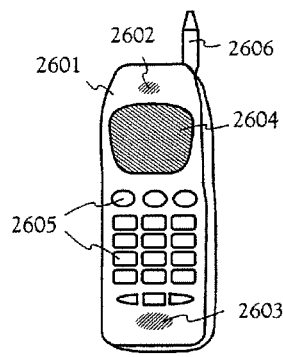
Figure 14:
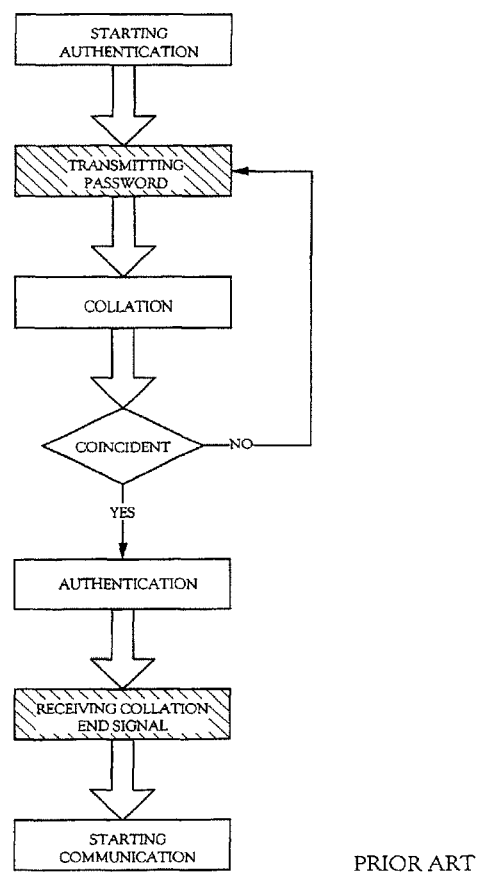
FIG. 14 is a flowchart showing the flow of an authentication processing according to the prior art.

FIG. 13B depicts a cellular telephone. It includes a main body 2601, a speech output part 2602, a speech input part 2603, a display part 2604, operation keys 2605, an antenna 2606, and so forth. When an ordinary call is made, the telephone number of the mating party and the reception condition of the radio wave are displayed on the display part 2604. When the Internet is used, the necessary information of the mating party is displayed. The display part 2604 serves also as the sensor and can acquire the living body information.

The display part 2604 of the cellular telephone shown in FIG. 13B has the function as the sensor and the function as the display. However, the sensor may be separately provided while the display part 2604 is utilized only as the display.

The authentication apparatus used in the present invention is not limited to the electronic apparatuses represented in the embodiments. Any device may be used so long as it can collate the living body information with the living body information stored in advance, and can notify the mating party of the end of authentication when collation proves coincident.

Since the present invention executes authentication by using the living body information, the present invention can eliminate the possibility that the password leaks to the third party other than the authentic person and authentication as the authentic person cannot be made. Therefore, the present invention can improve reliability of authentication of the user as being the authentic person.

Because the number of times of the data exchange operations for authentication can be restricted between the user and the mating party (or the manager), the present invention can restrict the cost necessary for transmitting and receiving the data, and can avoid the trouble of repeating once again from the beginning the authentication operation even when the communication is cut off for some reason or other.

Because the present invention executes authentication by using the living body information of the user, it is not necessary for the user to inquire of the mating party the password or to frequently re-write the password when the user forgets the password.

The information quantity of the living body information is generally greater than that of the password. However, because the present invention need not directly transmit the living body information of the authentic person or the user as the data to the mating party (or the manager), the present invention can limit the length of the time necessary for transmitting and receiving the data with the mating party (or the manager), and can also limit the cost.

In the present invention, it is not necessary to store the reference living body information of all the persons who execute authentication in the mating party (or the manager). Therefore, even when the information quantity of the living body information is greater than that of the password, the load to the mating party (or the manager) does not become great. Since the reference living body information is stored for each person, the number of reference living body information (in this case, all living body information of one person is counted as 1) when security is broken can be kept at a smaller value than when the reference living body information of all the persons who execute authentication is stored in the mating party (or the manager).

What is claimed is:

1. An information terminal comprising:
   a non-volatile memory for storing a reference living body information;
   a display in which a sensor is incorporated, the display being configured to display an image and the sensor being configured to read a collation living body information of a user;
   a collation circuit part for collating the collation living body information with the reference living body information; and
   an A/D converter, a digital signal processor, and a comparison circuit in the collation circuit part,
   wherein the sensor is further configured to adjust luminance of the display,
   wherein the A/D converter is arranged to convert the collation living body information into digital signals,
   wherein the digital signal processor is arranged to receive the digital signals and convert the digital signals to numerical values,
   wherein the comparison circuit is arranged to compare and collate the collation living body information converted to the numerical values with the reference living body information,
   wherein the reference living body information is a fingerprint, a palm print or a voiceprint, and
   wherein the collation living body information is a fingerprint, a palm print or a voiceprint.

2. The information terminal according to claim 1, further comprising an operation key and a control microcomputer,
   wherein the control microcomputer is arranged to control the sensor with an operation of the operation key.

3. The information terminal according to claim 1, wherein the collation is performed by an image matching system or a feature collation system.

4. The information terminal according to claim 1, further comprising:
   a signal processing circuit for compressing or expanding signals and encoding signals; and
   a transmission/reception circuit,
   wherein a notice of coincidence is outputted from the information terminal through the signal processing circuit and the transmission/reception circuit.

5. The information terminal according to claim 1, wherein a notice of coincidence is transmitted through Internet.

6. The information terminal according to claim 1, further comprising:
   a signal processing circuit for compressing or expanding signals and encoding the signals;
   a microphone;
   a speech input circuit;
   a speech output circuit; and
   a speaker.

7. The information terminal according to claim 1, further comprising an antenna, wherein the antenna is configured to transmit a notice of coincidence as data to a mating party or a manager when a collation result proves coincident.

8. The information terminal according to claim 1, wherein the reference living body information is a voiceprint, and wherein the collation living body information is a voiceprint.

9. The information terminal according to claim 1, wherein the sensor is further configured to measure brightness around the information terminal.

10. The information terminal according to claim 1, wherein the sensor is further configured so that the adjustment of the luminance is performed on the basis of brightness around the information terminal.

11. A cellular telephone comprising:
    a non-volatile memory for storing a reference living body information;
    a display in which a sensor is incorporated, the display being configured to display an image and the sensor being configured to read a collation living body information of a user;
    a collation circuit part for collating the collation living body information with the reference living body information; and
    an A/D converter, a digital signal processor, and a comparison circuit in the collation circuit part,
    wherein the sensor is further configured to adjust luminance of the display,
    wherein the A/D converter is arranged to convert the collation living body information into digital signals,
    wherein the digital signal processor is arranged to receive the digital signals and convert the digital signals to numerical values,
    wherein the comparison circuit is arranged to compare and collate the collation living body information converted to the numerical values with the reference living body information,
    wherein the reference living body information is a fingerprint, a palm print or a voiceprint, and
    wherein the collation living body information is a fingerprint, a palm print or a voiceprint.

12. The cellular telephone according to claim 11, further comprising an operation key and a control microcomputer,
    wherein the control microcomputer is arranged to control the sensor with an operation of the operation key.

13. The cellular telephone according to claim 11, wherein the collation is performed by an image matching system or a feature collation system.

14. The cellular telephone according to claim 11, further comprising:
    a signal processing circuit for compressing or expanding signals and encoding signals; and
    a transmission/reception circuit,
    wherein a notice of coincidence is outputted from the cellular telephone through the signal processing circuit and the transmission/reception circuit.

15. The cellular telephone according to claim 11, wherein a notice of coincidence is transmitted through Internet.

16. The cellular telephone according to claim 11, further comprising:
    a signal processing circuit for compressing or expanding signals and encoding the signals;
    a microphone;
    a speech input circuit;
    a speech output circuit; and
    a speaker.

17. The cellular telephone according to claim 11, further comprising an antenna, wherein the antenna is configured to transmit a notice of coincidence as data to a mating party or a manager when a collation result proves coincident.

18. The cellular telephone according to claim 11, wherein the reference living body information is a voiceprint, and wherein the collation living body information is a voiceprint.

19. The cellular telephone according to claim 11, wherein the sensor is further configured to measure brightness around the cellular telephone.

20. The cellular telephone according to claim 11, wherein the sensor is further configured so that the adjustment of the luminance is performed on the basis of brightness around the cellular telephone.

* * * * *